(12) United States Patent
Brovold et al.

(10) Patent No.: US 6,595,068 B2
(45) Date of Patent: Jul. 22, 2003

(54) COMPACT HOLLOW CYLINDER TENSILE TESTER

(76) Inventors: Thomas E. Brovold, 5330 Frane Ave. South, Apartment 105, Edina, MN (US) 55410-2008; William G. Buttlar, 604 Indigo Ave., Savoy, IL (US) 61874

( * ) Notice: Subject to any disclaimer, the term of this patent is extended or adjusted under 35 U.S.C. 154(b) by 0 days.

(21) Appl. No.: 09/791,160

(22) Filed: Feb. 22, 2001

(65) Prior Publication Data

US 2001/0037687 A1 Nov. 8, 2001

Related U.S. Application Data

(60) Provisional application No. 60/184,966, filed on Feb. 25, 2000.

(51) Int. Cl.$^7$ .................................................. G01N 3/00
(52) U.S. Cl. .......................................... 73/803; 73/807
(58) Field of Search ........................... 73/781, 784, 786, 73/788, 789, 796, 803, 804, 831, 887

(56) References Cited

U.S. PATENT DOCUMENTS 3,992,928 A * 11/1976 Thoms ........................ 73/784
4,653,331 A * 3/1987 Inouye et al. .................. 73/800
4,658,861 A * 4/1987 Roberson, Sr. ............... 138/90
5,969,242 A * 10/1999 Hubbell et al. ......... 166/250.03

* cited by examiner

*Primary Examiner*—Max Noori
(74) *Attorney, Agent, or Firm*—Oppenheimer Wolff & Donnelly LLP

(57) ABSTRACT

A hollow cylindrical tester uses an inflatable membrane to apply hoop stress to a hollow cylindrical sample. The compact device includes a frame that holds a sample around the inflatable membrane. The membrane is preferably inflated via fluid pressure and the fluid pressure preferably is monitored to determined pressure at critical points in testing procedures. Pressures of fluids within the membrane are also monitored. In a preferred structure, a piston and cylinder pressure injector operatively connected to the membrane is monitored for amount of piston travel and a pressure meter monitors fluid pressure. The preferred structure includes shaped opposing platens to seal the membrane within a cylinder sample being tested, a post failure restraint cylinder, and a cooling fluid bath.

43 Claims, 5 Drawing Sheets

COMPACT HOLLOW CYLINDER TENSILE TESTER

This application claims priority from Provisional Application Ser. No. 60/184,966, filed on Feb. 25, 2000.

FIELD OF THE INVENTION

The present invention relates generally to tensile testing of various material samples, to determine the suitability of modern pavement mixtures.

BACKGROUND OF THE INVENTION

Road building and repair is an extremely expensive and disruptive task. In response to such concerns, Congress funded, in 1987, a research program meant to improve the durability and performance of United States roads. Longevity and safety are the primary directives of the research program. Obviously, roads which have a longer useful life reduce maintenance and reconstruction expenses. Roads which resist cracking, buckling, rutting and holing also have clear safety advantages.

Superpave™ (a trademark of the Strategic Highway Research Program) is a product of research funded through this program. The pavement system optimizes asphaltic concrete pavement mixes to control undesired rutting, low temperature cracking and fatigue cracking. Development and installation of such pavements requires testing to obtain fundamental properties of the materials. Other construction techniques also require extensive material testing. Sampling of various concretes and other materials used in building construction ensures that engineering requirements and code requirements for the materials are maintained through building construction.

Tensile creep compliance, a temperature and loading time dependent stress-strain property, and tensile strength are important qualities of the asphaltic concrete mixtures developed under the highway initiative program. These properties are used with commercially available software to design and proportion asphalt concrete mixtures to be resistant to thermally-induced cracking. An Indirect Tensile Tester (IDT) has been approved by the Federal Highway Administration (FHWA), and has been the sole available test to provide required material property inputs for available thermal cracking performance prediction models contained in the FHWA's Superpave™ system and specification for designing high-quality asphalt paving mixtures.

The IDT is an expensive machine, costing approximately $140,000. This makes it one of the more expensive of the machines used to determine other characteristics associated with the design and installation of Superpave™ mixtures. Related machinery such as a gyratory compactor, bending beam rheometer, dynamic shear rheometer and rotary viscometer, (all devices used to measure other various portions of mixture design specifications), have costs in the approximate $10,000 to $40,000 price range. The high price of the IDT is therefore a substantial barrier to its widespread use by contractors seeking to install Superpave™ concrete mixtures.

Price concerns might eventually be addressed using the IDT, but a more significant difficulty associated with it is its large and cumbersome nature, and the relatively high level of expertise necessary to operate it properly. The IDT works under indirect tension test principles, where compressive loads are applied along thin loading strips on opposite sides of a cylindrical specimen being tested. This compressive loading creates tensile stress on opposite sides of the test specimen. As a result, up to 700 pounds per square inch of tensile stress is required to break asphalt concrete specimens at low temperatures. The need to generate that level of stress makes use of an approximately 22,000 pound capacity load frame and controller necessary. While these contribute significantly to the expense of the device, they also cause it to be large and cumbersome. The IDT frame weights 22,000 lbs. by itself, and is over seven feet tall. This effectively limits its use to a stationary laboratory, as opposed to transportation to a relevant field location. In the laboratory, it occupies a significant amount of space.

The IDT also has operational difficulties. Its associated test procedure requires the careful mounting of four high sensitivity transducers on every specimen. Every specimen must also be carefully aligned in the loading frame. A refrigeration based cooling system typically requires about fifteen minutes to restabilize before each test. Mounting the specimen, mounting and electrically balancing the transducers, and allowing appropriate time intervals between tests has shown that the testing is limited to about 1 sample per hour or less. In addition, a skilled technician is required for specimen mounting, transducer mounting and electrical balancing.

Subsequent to the development of the present invention, a new standard was introduced for determining the compliance of various asphaltic mixtures with static creep requirements. Namely, a 4" cylinder is to be cored from a sample and appropriately tested. This is a radical departure from previous testing standards. Such tests can be performed on samples acquired in the field, however for purposes of testing new or raw materials such tests need to be performed on lab prepared specimens.

The need to obtain such specimens in the lab is not a new problem and various machines and methods presently exist that facilitate the creation of asphaltic samples. One such device is the Brovold Gyratory Compactor, manufactured and sold by Pine Instruments. Such a device produces a compacted cylindrical asphalt sample that may be tested for compliance with the various industry standards. The Gyratory Compactor will produce a cylindrical sample having an outer diameter greater than 4". Thus to perform the above mentioned static creep test a 4" cylinder is cored, thus leaving a cylindrical hoop. This is beneficial in that the compaction process will affect and modify the material at the outer circumference of the cylinder; thus the smaller cored sample has a more uniform density.

The difficulty is that asphalt mixtures are not homogeneous. Thus, the particular sample selected can vary the results. To perform all of the tests required, two samples (tensile creep compliance, static creep compliance) will need to be fabricated in the compactor. Thus, due simply to normal differences in the non-homogeneous asphalt mixture, the samples can be quite different. This makes use of the IDT (which now requires a second cylindrical sample) less desirable.

Furthermore, by its very nature the IDT can produce varying results on a given sample. As mentioned above, asphalt is not homogeneous. It is comprised of a plurality of particles ranging in size and configuration that are bonded together. The IDT effectively "samples" selected particles and effectively ignores the remainder. Force is applied along two linear strips that are opposite one another on the cylinder, thus compressing the cylinder. This will cause the cylinder to deform into an oval or elliptical configuration. The mounted transducers monitor the change in diameter along the compressing direction and along the expanding direction. However, this is only done at selected points along the cross section (2 points for each direction). Thus, even though force is applied along the entire height of the cylindrical sample, its effects are only monitored at a few points. Thus, unless such a cylinder universally responds uniformly to an applied force, the IDT results can be affected. Furthermore, differences in the particulate nature of the asphalt can cause unique deformations to occur which will not be observed with the IDT due to its limited number of measurement points. Thus, the points selected for measurement will actually affect the results obtained. In other words, the IDT is incapable of averaging deformation across the whole sample.

The IDT thus suffers in that it cannot effectively measure average changes throughout a given sample and such tests cannot be performed on the same sample material used in the various other creep performance tests.

SUMMARY OF THE INVENTION

Accordingly, there is a need for an improved sample tester which addresses problems encountered in previous testers. It is an object of the present invention to provide such an improved sample tester capable of performing tensile creep compliance and tensile strength testing. The improved tester of the present invention has clear applicability to Superpave™ testing procedures, as well as any construction or engineering analysis in which such material properties are relevant.

These and other needs and objects are met or exceeded by the present compact tensile tester. The compact device includes a frame that holds a hollow cylindrical sample around an inflatable membrane. The membrane is inflated via fluid pressure and the fluid pressure preferably is monitored to determine pressure at critical points in the testing procedures. Furthermore, characteristics of a pressure injector used to inflate the membrane are monitored. In a preferred structure, a piston and a cylinder pressure injector are operatively connected to the membrane and the injector is monitored for amount of piston travel. A pressure transducer monitoring fluid pressure, which correlates to the amount of force exerted on the sample is attached to the sample.

The structure includes shaped opposing platens to seal the membrane within a hollow cylinder sample being tested, a post failure restraint cylinder, and a cooling fluid bath. A computer can be connected to the pressure transducer to obtain values at specific critical testing points and calculate appropriate sample characteristics based upon the obtained values.

In operation, one of the platens is opened or removed to permit insertion of an appropriately dimensioned hollow cylindrical sample around the relaxed membrane. Due to the nature of the device, no careful alignment of the sample or sensors is required. Instead, the platen is closed, sealing the membrane in the inserted hollow cylindrical sample. While pressure in the membrane is monitored, it is inflated to place even hoop stress on the inner walls of the sample. In a sample failure test, the post failure restraint cylinder contains the sample. The device is quickly cycled for additional tests, in part due to its use of a relatively simple fluid cooling bath, but mainly due to the overall simplicity of the testing protocol and elimination of cumbersome positioning and sensor alignment procedures inherent in the prior art testing protocol.

In an alternative embodiment, various sensors are positioned on the hollow cylindrical sample to directly monitor the displacement. Thus, fluid pressure is used to exert a uniformly applied force across the whole of the specimen, but only point measurements are taken.

The present invention provides a method and apparatus for determining a sample's average response to uniformly applied forces. As expected, this provides more accurate and complete data than is obtainable with the IDT. For this reason alone, the HCT becomes more advantageous to use than the IDT. Another advantage is the ability to perform the tensile tests with the HCT as well as the various static tests on a single asphalt sample made from one iteration in a Gyratory Compactor. As explained above, the compactor produces an asphalt cylinder. From this, a 4" cylinder is cored and used for static testing. What remains is a hollow cylinder ideal for use in the HCT. Though the outer circumference of this hoop has been somewhat modified during the compaction process, this will have little or no effect on the HCT since force is being applied to the inner circumference and this is where a vast majority of the compression occurs. Thus, a single gyratory sample can be used for all of the various required tests.

BRIEF DESCRIPTION OF THE DRAWINGS

Other objects, features and advantages of the present invention will become apparent upon reading the following detailed description, while referring to the attached drawings, in which.

DETAILED DESCRIPTION OF PREFERRED EMBODIMENTS

The present invention provides a compact hollow cylindrical sample tester (HCT) suitable for Superpave™ testing procedures, as well as other material analysis testing procedures which require tensile stress, creep compliance, failure, and other similar determinations. In operation, an inflatable membrane evenly asserts hoop stress on the sample, and the pressure required to inflate the membrane for the test provides complete and accurate testing data for critical points in a testing procedure. Alternatively, direct measurement of the expanding cylinders are taken.

Figure 1:
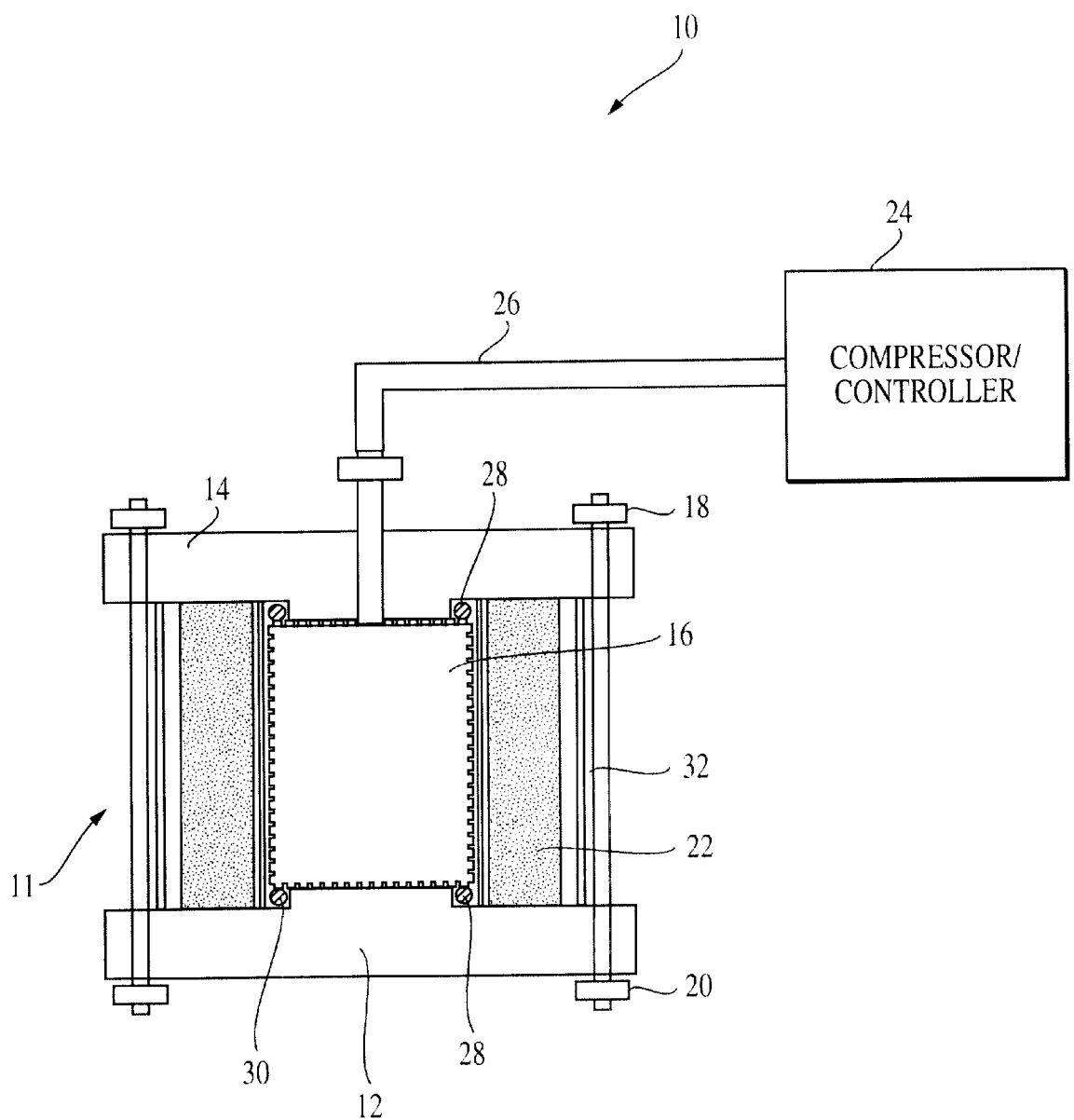
FIG. 1 is a side sectional view of a hollow cylindrical sample tester.

Turning to FIG. 1, a cutaway view of HCT 10 is shown. HCT 10 has a frame 11 composed of an upper platen 14 and a lower platen 12 which are coupled together with a plurality (two or more) of clamping rods 18. The clamping rods 18 in conjunction with a plurality of locking nuts 20 securely hold the platens 12,14 in this configuration.

A flexible membrane 16 is disposed between the upper platen 14 and the lower platen 12. The flexible membrane 16 is preferably made of rubber, however any suitably strong impermeable membrane is acceptable. As will be explained in more detail later, a fluid within the flexible membrane 16 becomes pressurized and exerts a force upon a rigid object, such as cylindrical sample 22. For purposes of the HCT 10, fluid is meant to include any liquid, gas or combination of the two. The cylindrical sample 22 will often be a material such as asphalt, or the like. The fluid within the flexible membrane is typically pressurized until the sample is caused to fracture. As such, the flexible membrane 16 must be able to withstand both the internal pressure exerted and the pressurized frictional engagement with the cylindrical sample 22. A restraint cylinder 32 surrounds the cylindrical sample 22, contains any fragmentation of the cylindrical sample 22, and prevents large openings from occurring in the sample 22 after the fracture.

A compressor/controller 24 is coupled to the frame 11 via a connection hose 26. The compressor 24 provides either the hydraulic or pneumatic force required to pressurize the flexible membrane.

In use, one or both of the platens 12,14 is separated from the frame 11. A hollow cylindrical sample 22 is placed about the flexible membrane 16 as shown. The platens 12,14 are then re-secured to the frame. The platens 12,14 are configured so as to support, but not restrain or exert a force on the cylindrical sample 22. This allows the cylindrical sample 22 to react freely to the force imparted by the flexible membrane 16. The primary purpose of the platens 12,14 is to prevent the flexible membrane 16 from expanding out beyond the top or bottom of the cylindrical sample 22. Therefore, in one embodiment, the platens 12,14 will not contact any portion of the cylindrical sample 22, but are simply configured to confine the flexible membrane 16. As shown in FIG. 1, a pair of O-rings 28 at the top and bottom of the flexible membrane 16 seal any gap that might exist between the membrane 16 and the sample 22. An additional protective film 30 may optionally be added between the cylindrical sample 22 and the flexible membrane 16. The protective film 30 is made of a material such as acetate, and serves to further protect the flexible membrane 16 from the abrasive contact generated during use of the HCT 10.

Figure 2:
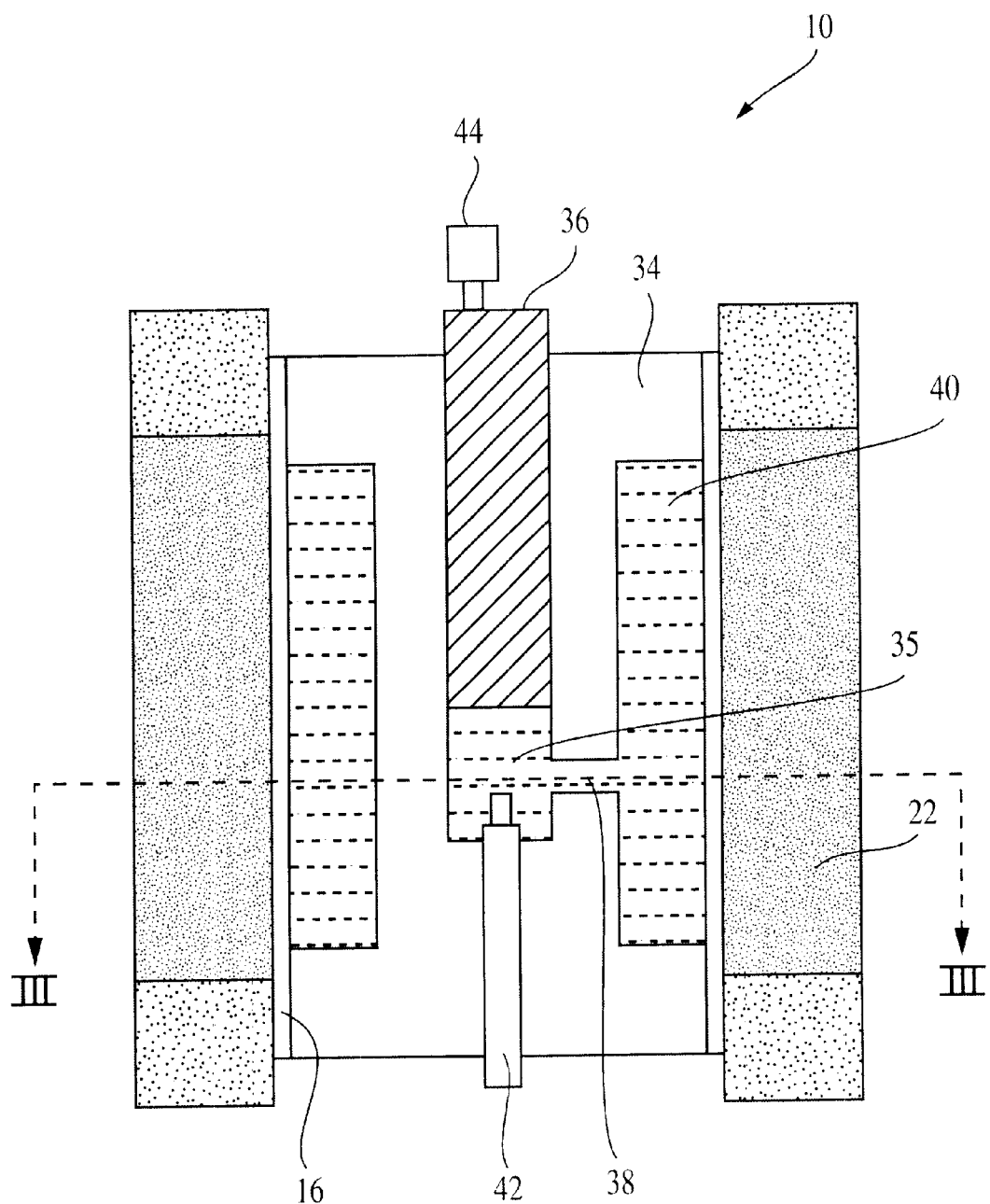
FIG. 2 is a sectional view of the hollow cylindrical sample tester including an intensifier within a cylindrical sample.

FIG. 2 is a cutaway view of the components within flexible membrane 16. As mentioned above, the HCT 10 obtains data about the cylindrical sample 22 by expanding the flexible membrane 16 inside the cylinder 22, and generating an outward force. By measuring the force exerted and the resulting structural changes in the sample 22, certain fundamental material properties are determined. To exert this force, the flexible membrane 16 is caused to expand by increasing the internal fluid pressure. This could be accomplished by simply pneumatically or hydraulically inflating the flexible membrane 16. Preferably, the flexible membrane 16 is filled with a (liquid) fluid 40. Compressed gas could be used instead, however in the event of an accidental rupture, the sudden release of the compressed gas would be more energetic and turbulent than a similar release of pressurized liquid. In either case, the volume of the gas or liquid may undergo substantial compression during the pressurization of the flexible membrane 16. This compression must be accounted for in any calculation of force or displacement. To minimize this factor, intensifier 34 is disposed within the core of the flexible membrane 16.

Intensifier 34 is a spool shaped rigid structure that is preferably made of metal. The intensifier 34 has a hollow inner chamber 35 which is fluidly connected to the interior of the flexible membrane 16 via drilled port 38. A pressure injector such as piston 36, also preferably made of metal, is disposed within the inner chamber 35. The piston 36 is moveable longitudinally within the inner chamber and is displaced by the compressor 24. As the piston 36 travels, it pressurizes the fluid 40. To some extent, the fluid 40 and the flexible membrane 16 will compress, however most of this pressure is translated into a force which is exerted on the cylindrical sample 22. The intensifier 34 serves to occupy a large percentage of the interior volume of the flexible membrane 16. This reduces the volume of fluid 40 which is required, thus minimizing the effect of the fluid compression on the final displacement calculations. It is desirable to not have any air present when liquid is being used as the medium. A valve or other release mechanism can be added in intensifier 34, piston 36 or any other convenient location in order to vent air or other gases that must be present. To facilitate this, the components illustrated in FIG. 2 can be inverted during fabrication or assembly in order to allow rising gases to be vented.

The piston 36 has a known surface area that is in contact with the fluid 40. The particular structure of the intensifier 34 allows for a relatively small (diameter) piston 36 to be used, however the same effect could be achieved without the intensifier 34 and using a larger piston. The movement of the piston 36 is monitored by a sensor, such as LVDT 44 (linear voltage differential transducer). The displacement of the piston 36 is correlated to the give of the cylindrical sample 22. As such, the pressurizing system of HCT 10 is also a measuring system. In one application, the amount of give allows for the calculation of the creep compliance of an asphalt cylinder. The LVDT 44 need only be a low sensitivity sensor, which allows for a minimization of costs.

A pressure meter such as pressure transducer 42 is mounted within the flexible membrane 16 adjacent to the intensifier 34. The pressure transducer 42 monitors the pressure exerted by the fluid 40 and from this, the amount of force exerted is calculable. As such, it is possible to determine the force exerted on the cylindrical sample 22 as well as the physical response of the cylindrical sample 22 with a single LVDT 44 and a single pressure transducer 42. This arrangement is particularly efficient in that the force imparted to the piston 36 is significantly less than the force that will be imparted to the sample 22. For example, applying 400 lbs. of force to the piston generates 700 lbs. of force (tensile/hoop stress) on the inner circumference of the sample 22. As is shown in FIGS. 1 & 2, the flexible membrane 16 is not in contact with the entire inner surface of the cylindrical sample 22. As explained above, this is done to prevent the flexible membrane 16 from expanding beyond the cylindrical sample 22. As a result, three dimensional finite analysis must be employed to determine the material properties of the cylindrical sample 22 based upon the force/displacement data generated.

Figure 3:
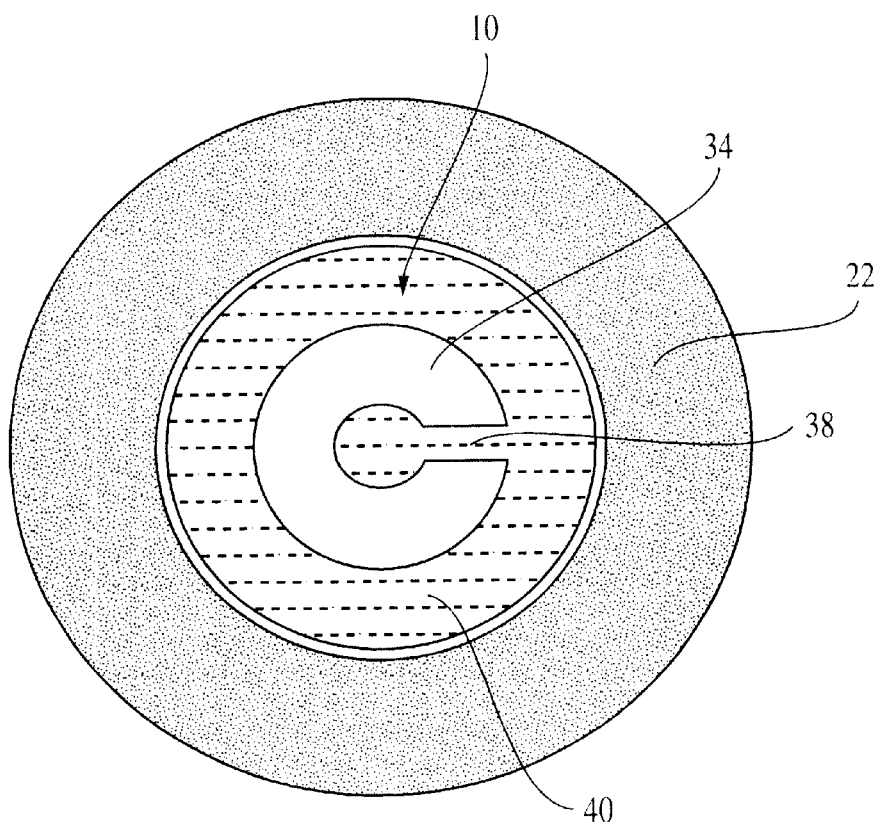
FIG. 3 is a sectional view of an HCT about line III—III in FIG. 2.

FIG. 3 is a top planar view of HCT 10 taken about sectional lines III—III. From this view is becomes apparent that the force exerted by the pressurized fluid is evenly distributed about the inner circumference of the cylindrical sample 22.

Figure 4:
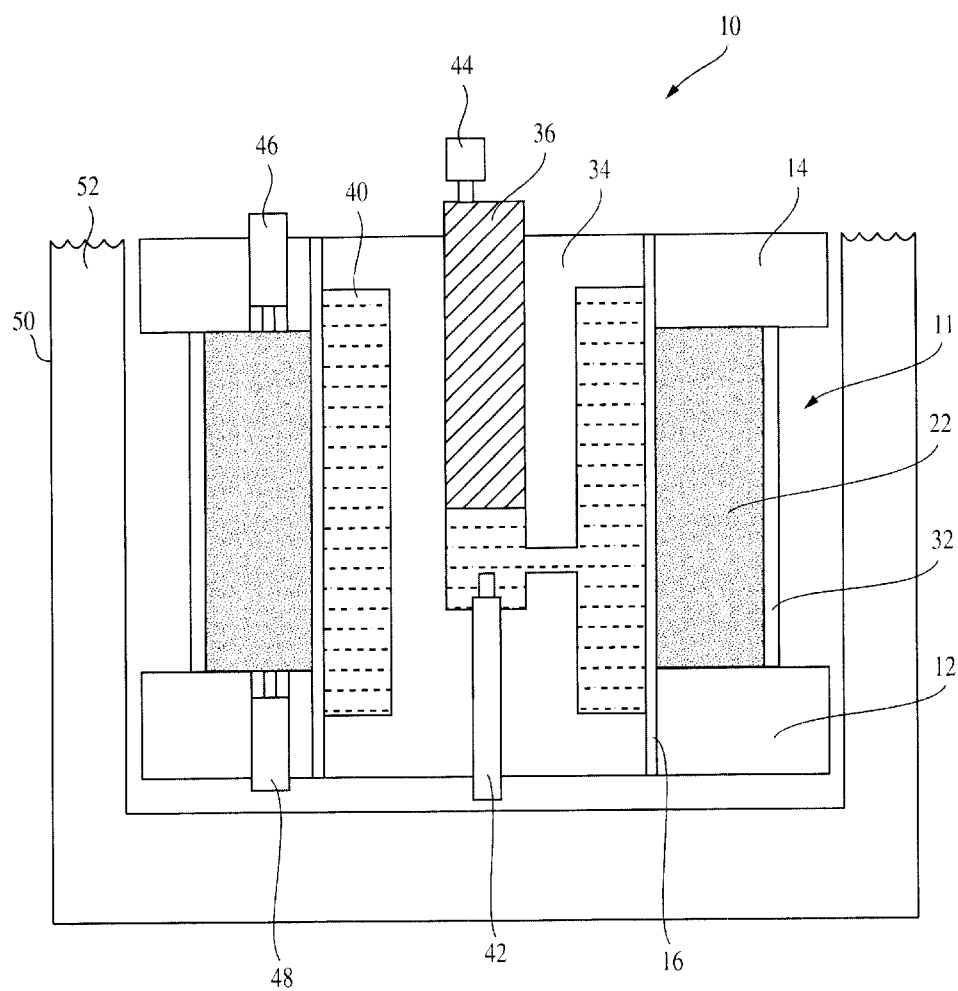
FIG. 4 is a sectional view of an HCT within a liquid cooling bath.

In FIG. 4, the frame 11 is surrounded by a cooling chamber 50. The cooling chamber 50 is filled with a liquid 52 that is maintained at a particular temperature. This effectively maintains the HCT 10 and the cylindrical sample 22 at this same temperature. This allows the HCT 10 to be used to measure specific material properties at preselected temperatures. The cooling chamber 50 allows for cylindrical samples 22 to be removed and replaced without a significant increase in thermal energy. That is, the temperature of the liquid 52 in the cooling chamber 50 can be efficiently maintained during the testing of multiples samples 22. Due to the efficiency of this arrangement, new samples 22 are brought to their preselected temperature relatively quickly, therefore allowing for the rapid testing of a large number of samples 22.

As the flexible membrane 16 expands, it will exert an outward force on the cylindrical sample 22. As this force increases, the cylindrical sample reacts by compressing (and eventually fracturing, if the force is sufficient). Concurrently, the height of the cylindrical sample 22 will decrease as a direct result of this outward expansion. This decrease in height is related to Poisson's ratio and may be measured by adding another LVDT 46 or 48 at either the top or bottom of the sample 22. As discussed later, one of the measurements that the HCT 10 is to obtain is the "creep compliance" of the cylindrical sample 22. Essentially, this amounts to the outward expansion of the cylindrical sample 22 under a constant force. The decrease in height will add a certain degree of error to the determination of the creep compliance. The LVDT 46 or 48 can measure the change in height and from this data, that error can be eliminated in the creep compliance determination. As a practical matter, the error introduced by the vertical contraction is minor and may be ignored without seriously affecting the results. Thus LVDT's 46 or 48 are entirely optional.

While the HCT 10 can be used to measure the fundamental physical properties of cylinders of any type of material, the primary purpose of the described embodiment is to test asphalt mixtures which are to be used in the Superpave™ program. Within this program, certain standards have been implemented. For example, the various mixtures which are to be used are placed within a gyratory compactor which forms uniform cylinders. These cylinders are typically 115 mm in height and have an outside diameter of 150 mm. The cylindrical wall will usually be about 1 inch thick (about 50 mm). The HCT 10 is sized to accommodate these standard cylinders.

In use, the fluid 52 in the cooling chamber 50 is brought to a predetermined temperature (+/−0.2°). For compliance with Superpave™ requirements, the asphalt mixtures must perform adequately under low temperature thermal stresses. Therefore, the mixtures are tested at 0° C., −10° C., and −20° C. for creep compliance and at 20°, 4°, 0°, −10° and −20° C. for tensile strength. As such, the cooling bath needs to have a temperature range of between +25° C. to −20° C.

It is critical to realize that asphalt behaves differently at lower temperatures than it does at higher temperatures. As such, entirely different tests (using different types of equipment) must be performed for high and low temperatures. The HCT is being utilized at low temperatures to test the creep compliance and tensile strength of asphalt mixtures.

When being set up for testing, one platen 12,14 is removed and a cylindrical sample 22 is slid over the flexible membrane 16. Due to the nature of the HCT 10 and the tests which are to be performed, no precise alignment is required. The removed platen 12,14 is then re-secured. The fluid 52 in the cooling chamber 50 maintains its temperature during the interchange of cylindrical samples 22, and serves to rapidly bring each new sample to the appropriate temperature.

Once the proper temperature is achieved, two types of tests are performed: a creep compliance test and a tensile strength test.

One of the primary concerns with asphalt paving is thermal cracking. When asphalt pavement is cooled, tensile stress develops. That is, the length of asphalt is held constant, and any contraction that occurs as it cools results in a developed strain. Thermal stresses develop because the pavement is forced to contract as the temperature lowers. Generally, pavement will not have joints added and must rely on the flexibility of the materials used to accommodate such contractions. Those tensile stresses can cause two types of problems. Thermal fatigue cracking occurs as a progressive and gradual crack propagation during temperature cycling. This problem can be predicted by testing and measuring the asphalt mixtures' creep compliance. The other problem occurs when asphalt pavement, which has been rapidly cooled, suddenly cracks. The propensity for a given asphalt mixture to behave like this is predicted by a tensile strength test.

To perform the creep compliance test, the piston 36 is rapidly actuated until the pressure transducer 42 determines that the pressurized fluid 40 is exerting a predetermined amount of force on the cylindrical sample 22. The purpose of this test is to exert a constant force on the sample 22 for a predetermined period of time and then to measure the resultant changes in the sample 22. Such a change will occur in the cylindrical sample 22 by the cylinder expanding outward (the cylinder wall will essentially compress). More specifically, the inner circumference compresses towards the outer circumference and to a lesser extent, the outer circumference may also expand. With no other change, the force exerted by the pressurized fluid 40 will be reduced because of the corresponding increase in volume generated by the cylinder's expansion. Therefore, as the cylinder 22 expands, the piston 36 must be further actuated to maintain a constant pressure (and hence, a constant force) on the volumetrically dynamic cylinder. This constant force is maintained for some predetermined amount of time. At the completion of that time period, the distance that the piston 36 has traveled, since first establishing the correct amount of force (as a starting point) until the point the piston 36 is at when the time period has expired (the finishing point), is measured. As a practical matter, the entire distance traveled by the piston 36 is monitored, however, only the distance traveled after establishing the predetermined pressure is relevant to this particular test. The additional data acquired may be useful in other calculations. For example, with uniform cylinders, the initial amount of travel will correlate to the pressure generated thus reducing the reliance placed upon the pressure transducer 42.

The distance is accurately measured by LVDT 44. Since the surface area of the piston 36 is known, the distance traveled corresponds to the change in the volume of the fluid 40 as the cylinder 22 expands. This change in volume is then translated into the corresponding "creep" of the asphalt cylinder. In other words, as the sample 22 deforms under stress, the additional amount of fluid 40 that would be required to maintain a constant pressure is accurately measured. Alternatively, fluid could be injected into the flexible membrane 16 to maintain the constant pressure. The amount of fluid added would be equal to the volumetric change in the sample 22. In this approach, piston 36 would remain stationary after establishing the starting pressure.

In theory, the creep compliance of any given asphalt mixture will predict how much a paved surface will give under a relatively constant load (within the predetermined temperature range). The HCT 10 is ideal for performing this test because of its configuration. That is tensile, or hoop, stresses are created evenly along the entire inner circumference of the asphalt cylinder 22, rather than at individual discrete points. Thus, almost the entire cylinder 22 is evenly subjected to the same stresses, which will produce more accurate and consistent results.

The HCT 10 is also used to perform tensile strength tests. This test determines the amount of force required to fracture the asphalt cylinder 22 at specific temperatures. Once a test cylinder 22 has been inserted and brought to the correct temperature, the piston 36 is actuated to increase the fluid pressure within the flexible membrane 16. Flexible membrane 16 is caused to expand uniformly and correspondingly exerts a force upon the inner circumference of the cylindrical sample 22. The pressure transducer 42 measures the pressure of the fluid 40, which corresponds to the force exerted upon the cylinder 22. The pressure is slowly and evenly increased until the cylinder 22 fractures. When this occurs, the restraint cylinder 32 contains the cylinder 22, thus preventing any large holes from forming or any debris from being ejected. When the cylinder 22 fractures, there will be a sudden decrease in the pressure recorded by pressure transducer 42. This indicates the completion of the test and the highest pressure recorded corresponds to the amount of force required to fracture the cylinder 22. The fluid 40, the flexible membrane 16, and any other compressible material disposed within the center of the cylindrical sample 22 can impart an error into the test results. That is, these various materials will undergo some amount of compression under pressure. This compression factor must be determined and removed from the pressure/force calculations. One way to accomplish this is to perform the test with a cylindrical sample 22 (having the same inner diameter but very thick walls) made from a very rigid material, such as steel. In this manner, the compressibility of the various materials is easily measured.

As mentioned above, in one embodiment the flexible membrane 16 is shorter than the height of the cylindrical sample 22. That is, there is a small portion of the interior of the cylindrical sample 22 which is not engaged by the flexible membrane 16. Due to this, the various force calculations discussed above become more difficult. To arrive at the proper results, three dimensional finite analysis must be employed to extract the fundamental physical properties of the cylindrical sample 22 from the data acquired from the various LVDTs and pressure transducers. Once so established, correction factors are determined which allow for the proper correlation between the closed form solution for the stressed cylinder and the data that is actually acquired.

While the present invention is used primarily to determine the tensile proportions of asphalt mixtures, it has many other practical applications. For example, the HCT 10 can be used to measure Poisson's ratio, resilient modulus, fracture toughness, fatigue resilience, and the moisture sensitivity of various types of materials. The HCT 10 is useful in determining such proportions in a wide variety of materials including, but not limited to: asphalt, ceramic, mortar, composites and polymers.

Figure 5:
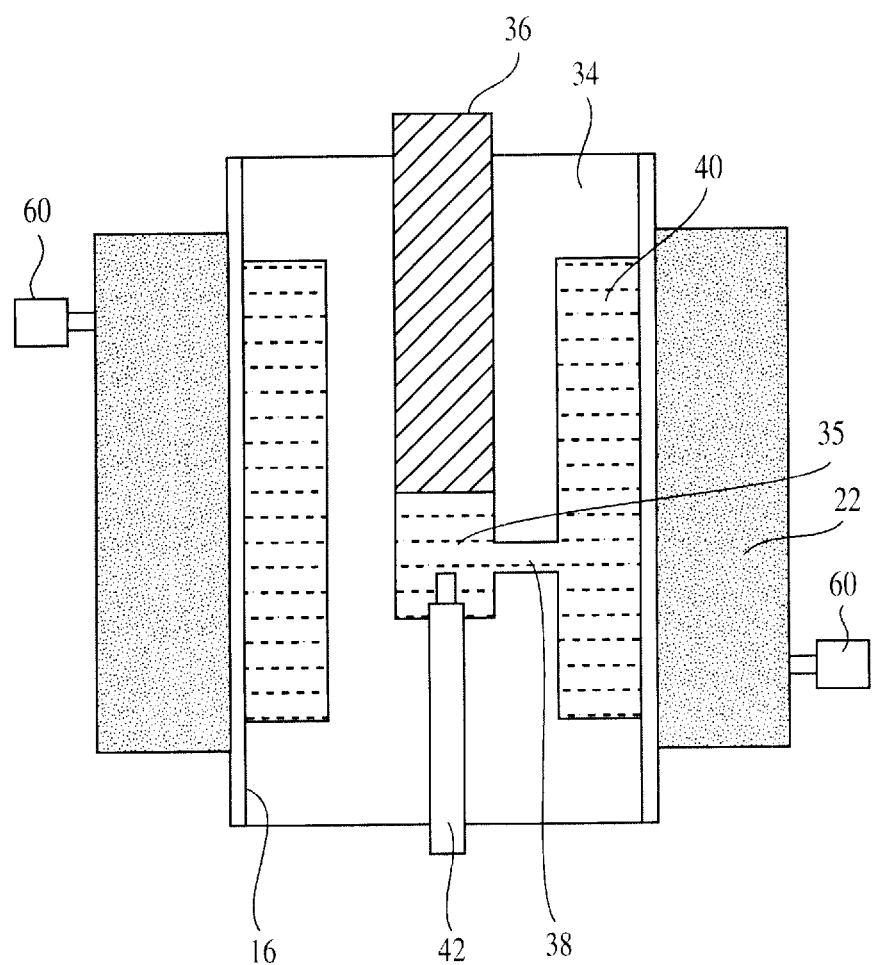
FIG. 5 is a sectional view of an HCT with external sensors mounted to detect deflection.

In an alternative embodiment, it is possible to obtain direct measurements of the resultant changes in cylindrical sample 22. Referring to FIG. 5, the general concept is illustrated. Rather than measuring the change in volume in fluid 40, various sensors 60 can be positioned to monitor changes in the diameter over sample 22. Though not separately shown, sensors 60 could also be used to take "before" and "after" measurements of the internal dimensions of cylindrical sample 22. There is no limit to the number of measurement points that can be obtained. Directly measuring sample 22 will not provide as averaged a result as measuring the volumetric change, but does produce an easier system to assemble and utilize. The results achieved will still be dramatically improved from devices such as the IDT because the force is still uniformly and evenly applied to the whole of the sample. Sensors 60 can be any electronic or mechanical measuring device (such as a LVDT) having a sufficient degree of accuracy.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited in the particular embodiments which have been described in detail therein. Rather, reference should be made to the appended claims as indicative of the scope and content of the present invention.

What is claimed is:

1. A hollow cylinder tensile tester for testing a hollow cylindrical sample, the tester comprising;
    an inflatable membrane placeable within a central area of the hollow cylindrical sample, the inflatable membrane having a contained area therein;
    a pressure meter, said meter operatively placed to determine pressure within said contained area;
    a pressure injector operatively connected with said membrane so as to establish and maintain a constant pressure within said contained area; and
    a transducer for measuring the movement of the pressure injector, wherein the measurement of the movement of the pressure injector correlates to a volumetric change of the contained area.

2. The tester according to claim 1, further comprising an intensifier integrated within the membrane to reduce a compressible volume of the contained area.

3. The tester according to claim 2 wherein the pressure injector is moveable within the intensifier.

4. The tester according to claim 3 wherein the pressure injector increases pressure within the intensifier, and the intensifier is fluidly connected to the contained area within the membrane.

5. A tester according to claim 1, wherein a frame accommodates the cylindrical sample and the cylindrical sample has an outside diameter of about 150 mm, an inside diameter of about 100 mm and a height of about 115 mm.

6. A tester according to claim 1, wherein said membrane is shaped to expand and contact an inner wall of said hollow cylindrical sample throughout a circumference of said inner wall.

7. A tester according to claim 6 further including a frame having a pair of platens disposed to contain said membrane within the hollow cylinder sample during inflation of the membrane by closing open ends of the hollow cylinder sample.

8. A tester according to claim 1, wherein said pressure injector comprises:
    a cylindrical housing having a chamber operatively connected to said membrane through a port in said housing;
    a piston within said cylindrical housing;
    a power source for driving said piston.

9. A tester according to claim 8, wherein said transducer measures travel of said piston to permit calculation of volumetric change by an amount of measured piston travel.

10. A tester according to claim 8, wherein said membrane has fluid therein.

11. A tester according to claim 10, wherein said pressure meter monitors fluid pressure.

12. A tester according to claim 1, further comprising a fluid bath to control temperature of the cylindrical sample.

13. A tester according to claim 1, further comprising:
    opposing platens held apart at a predetermined distance by a frame, at least one of said platens being removable connected to said frame; and a restraint cylinder dimensioned to sealingly contain the hollow cylindrical sample between said platens.

14. A tester according to claim 13, wherein said platens each include a raised portion which extends partially into said restraint cylinder and a seal adjacent a sidewall of said raised portion.

15. A tester according to claim 13, further comprising a protective film which surrounds said membrane.

16. A method for measuring fundamental physical characteristics of materials comprising:
   placing a cylinder of the material over an inflatable membrane;
   expanding the inflatable membrane so as to increase an internal pressure therein to a predetermined level that exerts a force on an interior circumference of the cylinder;
   measuring the pressure generated within the expanding membrane and determining an amount of force exerted;
   maintaining a predetermined level of pressure for a predetermined amount of time;
   monitoring the cylinder for a diametric reaction to the force generated for the predetermined amount of time; and
   correlating the diametric reaction of the cylinder and the force generated to determine fundamental physical characteristics of the cylinder.

17. The method of claim 16 further comprising:
   filling the inflatable membrane with a fluid prior to expanding the membrane.

18. The method of claim 16 further comprising:
   placing an intensifier within the inflatable membrane to reduce the compressible volume of an interior of the inflatable membrane.

19. The method of claim 16, further comprising:
   actuating a piston to expand the inflatable membrane and maintain the predetermined level of pressure;
   measuring an amount of piston travel which occurs during the predetermined amount of time;
   calculating the volumetric change in the inflatable membrane based upon the amount of piston travel;
   determining an amount of creep for the cylinder based upon the calculation of volumetric change.

20. The method of claim 16, further comprising:
   actuating a piston at a constant rate to increase the internal pressure within the inflatable membrane until the cylinder fractures;
   monitoring the pressure within the membrane until the fracture occurs;
   determining the tensile strength of the cylinder based upon the force exerted by the inflatable membrane at the time of fracture.

21. The method of claim 16 further comprising:
   removing a factor of the compressibility of the membrane and any compressible elements within it, from the correlation of physical characteristics.

22. The method of claim 16, further comprising:
   actuating a piston to expand the inflatable membrane and maintain the predetermined level of pressure;
   measuring an amount of movement in the cylinder by placing sensors in contact with the cylinder;
   determining an amount of creep for the cylinder based upon the measured amount of movement.

23. The method of claim 22 wherein measuring the amount of movement includes:
   placing at least one sensor in contact with the cylinder during measurement period.

24. The method of claim 23 wherein measuring the amount of movement includes:
   measuring an interior diameter of the cylinder before the measurement period; and
   measuring the interior diameter of the cylinder after the measurement period.

25. The method of claim 16 wherein the material is asphalt.

26. The method of claim 16 wherein the material is an asphalt mixture.

27. A hollow cylinder tensile tester for testing a hollow cylindrical sample, the tester comprising:
   an inflatable membrane placeable within a central area of the hollow cylindrical sample; the inflatable membrane having a contained area therein;
   a pressure meter, said meter operatively placed to determine pressure within said contained area;
   a pressure injector operatively connected with said membrane so as to establish and maintain a constant pressure in said contained area; and
   a sensor for measuring the cylindrical sample.

28. The tester according to claim 27, further comprising an intensifier integrated within the membrane to reduce a compressible volume of the contained area.

29. The tester according to claim 28 wherein the pressure injector is moveable within the intensifier.

30. The tester according to claim 29 wherein the pressure injector increases pressure within the intensifier, and the intensifier is fluidly connected to the contained area within the membrane.

31. A tester according to claim 27, further comprising a frame that accommodates a sample having an outside diameter of about 150 mm, an inside diameter of about 100 mm and a height of about 115 mm.

32. A tester according to claim 27, wherein said membrane is shaped to expand and contact an inner wall of said hollow cylindrical sample throughout a circumference of said inner wall.

33. A tester according to claim 32, said frame further comprises a pair of platens disposed to contain said membrane within the hollow cylinder sample during inflation of the membrane by closing open ends of the hollow cylinder sample.

34. A tester according to claim 27, wherein said pressure injector comprises:
   a cylindrical housing having a chamber operatively connected to said membrane through a port in said housing;
   a piston within said cylindrical housing;
   a power source for driving said piston.

35. A tester according to claim 34, wherein said sensor measures a diameter of the sample.

36. A tester according to claim 35, wherein the diameter measured is an outer diameter.

37. A tester according to claim 35 wherein the diameter measured is an interior diameter.

38. A tester according to claim 35, wherein said membrane has fluid therein.

39. A tester according to claim 27, wherein said pressure meter monitors fluid pressure.

40. A tester according to claim 27, further comprising a fluid bath to control temperature of the cylindrical sample.

41. A tester according to claim 27, further comprising:

opposing platens held apart at a predetermined distance by a frame, at least one of said platens being removable connected to said frame; and a restraint cylinder dimensioned to sealingly contain the hollow cylindrical sample between said platens.

42. A tester according to claim 41, wherein said platens each include a raised portion which extends partially into said restraint cylinder and a seal adjacent a sidewall of said raised portion.

43. A tester according to claim 41, further comprising a protective film which surrounds said membrane.

* * * * *